(12) United States Patent
Teichman et al.

(10) Patent No.: US 7,599,727 B2
(45) Date of Patent: Oct. 6, 2009

(54) LIGHTING AND IMAGING SYSTEM INCLUDING A FLAT LIGHT SOURCE WITH LED ILLUMINATION

(75) Inventors: Eyal Teichman, Hod-Hasharon (IL); Avner Schrift, Rishon-Le-Zion (IL)

(73) Assignee: Labcoat, Ltd., Galway (IE)

( * ) Notice: Subject to any disclaimer, the term of this patent is extended or adjusted under 35 U.S.C. 154(b) by 541 days.

(21) Appl. No.: 11/227,767

(22) Filed: Sep. 15, 2005

(65) Prior Publication Data

US 2007/0073134 A1    Mar. 29, 2007

(51) Int. Cl.
*A61B 5/05* (2006.01)
*G06K 9/00* (2006.01)
*G01N 21/47* (2006.01)

(52) U.S. Cl. .............. 600/407; 382/128; 382/130; 356/446

(58) Field of Classification Search .......... 600/407, 600/476, 430, 473; 362/257, 227; 382/152, 382/141, 128, 130; 356/601, 429, 237.2, 356/445, 446, 237.6; 700/95; 623/1.15
See application file for complete search history.

(56) References Cited

U.S. PATENT DOCUMENTS

| | | | |
|---|---|---|---|
| 5,153,668 A | | 10/1992 | Katzir et al. |
| 5,964,751 A | * | 10/1999 | Amplatz et al. ............... 606/15 |
| 5,984,493 A | * | 11/1999 | Higgins et al. .............. 362/283 |
| 6,259,827 B1 | | 7/2001 | Nichani |
| 6,606,403 B2 | | 8/2003 | Freifeld |
| 2005/0151979 A1 | | 7/2005 | Siekmeyer |

FOREIGN PATENT DOCUMENTS

| | | |
|---|---|---|
| EP | 0732084 A1 | 9/1996 |
| EP | 1 274 251 | 1/2002 |
| JP | 2001 070455 | 3/2001 |
| WO | WO 2004/012784 | 12/2004 |

* cited by examiner

*Primary Examiner*—Eric F Winakur
*Assistant Examiner*—Katherine L Fernandez
(74) *Attorney, Agent, or Firm*—Vidas, Arrett & Steinkraus, P.A.

(57) ABSTRACT

A system for lighting a stent, i.e., providing an illumination source, to facilitate the capturing of an image of the stent. The lighting is provided so that an image capturing device, e.g., a digital camera or system, will capture an image that distinctly shows the difference between the stent and any surface upon which the stent is mounted, in addition to sharply defining the edges of the stent struts.

8 Claims, 8 Drawing Sheets

LIGHTING AND IMAGING SYSTEM INCLUDING A FLAT LIGHT SOURCE WITH LED ILLUMINATION

FIELD OF THE INVENTION

The present invention is directed generally to illuminating an object in order to capture an image of that object. More specifically, a lighting system is provided to capture an image of a stent mounted on a supporting fixture in order to identify stent strut edges and surfaces.

BACKGROUND OF THE INVENTION

The practice of coating an implantable medical device, such as a stent, with a synthetic or biological active or inactive agent is known. Numerous processes have been proposed for the application of such a coating, for example: soaking or dipping the implantable device in a bath of liquid medication; soaking the device in an agitated bath; and spraying the medication on to the device by way of pressurized nozzles.

Initially, such coatings were applied at the time of manufacture of the medical device. The short shelf life of some drugs, combined with the time span from manufacture to implantation, and the last minute dosage decision concerning a specific drug to be used based on a patient's condition at the time of implantation, have contributed to a need for technologies that permit applying a coating just prior to implantation. These "just in time" approaches include: wrapping the implantable device with medicated conformal film; dipping or soaking in a medicated bath just prior to implantation; and providing a bathing chamber for use with a specific implantable device such as a stent deployed on the balloon of a catheter.

Each of the methods and devices intended for use just prior to implantation, listed above, however, deposits the coating material onto any and all surfaces that are exposed to the coating. This may result in depositing coating material on surfaces on which the coating is unwanted or undesirable. Further, the coating may crack or break away when the implantable device is removed from the implantation apparatus. This cracking may occur on a stent deployed on a catheter balloon. As the balloon is inflated, and the stent is expanded into position, the coating may crack along the interface between the stent and the balloon. These cracks may lead to a breaking away of a portion of the coating from the stent itself. Similar problems can occur in cases where the coating technique fails to prevent inadvertent overlapping with the internal surfaces along the edges of various devices, e.g., struts of stents. This, in turn, may affect the medicinal effectiveness of the coating, and negatively affect the entire medical procedure.

It is known to use ink-jet technology to apply a liquid to selected portions of a surface. In one instance, the selective application of the material is based on an objective predetermined location for deposit rather that on a "subjective placement" as needed to meet the requirements of a specific application procedure. With regard to the application of coatings applied to medical devices with inkjet applicators, it is possible to coat only a chosen portion of a device, such as only the stent mounted on a catheter, but not the catheter itself. This type of procedure using current technologies may, however, require, for example, providing complex data files, such as a CAD image of the device to be coated, and insuring that the device is installed in the coating apparatus in a precise manner so as to be oriented exactly the same as the CAD image.

Alternatively, a real-time picture can be taken with a camera to determine the position of the ink-jet nozzle in relation to the prosthesis. Based upon the feedback of nozzle location, the ink-jet applicator can be controlled by activating the spray, moving the ink-jet nozzle, and/or moving the prosthesis to adjust to the pattern to better conform with the actual prosthesis.

To apply a coating to a stent, it is necessary to distinguish the stent from any surface upon it which might be mounted, e.g., a mandrel or a balloon catheter, and account for configurations that might not be predicted from information such as CAD drawings. Further, it is necessary to distinguish between the struts of the stent and the interstitial spaces so as not to apply coating in the spaces. Being able to distinguish between the spaces and the struts reduces the amount of "wasted" coating material as well as prevents, in the case of a balloon-mounted stent, placing coating material on the balloon surface.

SUMMARY OF THE INVENTION

The present invention is a system for lighting a stent, i.e., providing an illumination source, to facilitate the capturing of an image of the stent. The lighting is provided so that an image capturing device, e.g., a digital camera or system, will capture an image that distinctly shows the difference between the stent and any surface upon which the stent is mounted, in addition to sharply defining the edges of the stent struts.

In one embodiment, a method includes mounting an item on a supporting structure, the supporting structure comprising material through which some light can pass; providing a source of illumination; illuminating a first side of the mounted item with the illumination source; and capturing an image of the mounted item from an image capturing position located opposite the first side of the mounted item along an optical axis. The image capturing position, the mounted item and the source of illumination are substantially aligned along the optical axis and the mounted item is located between the image capturing position and the source of illumination.

In the captured image, a portion of the image attributable to the item appears darker than a portion of the image attributable to the supporting structure.

In one embodiment, the mounted item is a stent; and the supporting structure is a balloon catheter having a balloon portion on which the stent is mounted, the balloon portion comprising a light diffusing material. The source of illumination may be located within the balloon catheter.

In another embodiment, a system includes: a supporting structure comprising material through which some light can pass; an item mounted on the supporting structure; a light source to provide illumination to a first side of the mounted item; and an image capturing device located opposite the light source such that the mounted item is located between the image capturing device and the light source. The image capturing device, the mounted item and the light source are substantially linearly aligned along an optical axis.

In yet another embodiment in accordance with one aspect of the present invention, a system includes: a supporting structure; an item mounted on the supporting structure; a beam splitter; a direct light source to direct light along a light axis through the beam splitter to illuminate the supporting structure and the mounted device; a second light source to illuminate the supporting structure and the mounted item with diffuse light, the second light source positioned to provide the diffuse light symmetrically about the light axis; and an image capturing apparatus positioned to capture light reflected by the beam splitter, the light provided to the image capturing apparatus being light reflected by the mounted item and the supporting structure back along the light axis.

An angle of coverage of the second light source is in a range of 80° to 120°.

In another embodiment, the system incorporates: a first mirror; and a second mirror disposed opposite the first mirror and symmetrically about the light axis. In operation, the first and second mirrors reflect higher angle diffuse light from the second light source onto the item and the supporting structure.

The mounted device may be a stent; and the supporting structure may be a balloon catheter having a balloon portion on which the stent is mounted, the balloon portion comprising a light diffusing material.

In yet another embodiment of the present invention, a method of determining characteristics of a portion of a mounted device assembly, the mounted device assembly comprising a device mounted on a support structure is provided. The method comprises: capturing a first image of the assembly at a first angular position; storing a central portion of the first image; rotating the assembly a predetermined angular amount to a second angular position; capturing a second image of the assembly at the second angular position; identifying pixels in the second image that correspond to pixels in the central portion of the first image; comparing the identified pixels in the second image to the corresponding pixels in the central portion of the first image; and determining the characteristics of the assembly as a function of the comparison.

In another aspect of the present invention, the identified pixels in the second image are of a first image type and the corresponding pixels in the central portion of the first image are of a second image type and the identified pixels in the second image and the corresponding pixels in the central portion of the first image each correspond to a same portion of the assembly and the method further comprises: determining that the corresponding portion of the assembly has a first characteristic when the first and second image type are the same; and determining that the corresponding portion of the assembly has a second characteristic when the first and second image type are different.

The assembly may comprise: a balloon catheter having a balloon portion; and a stent mounted on the balloon portion of the balloon catheter. Further, it is determined that the corresponding portion of the assembly is a part of the stent when each of the first and second image type is bright; or the corresponding portion of the assembly is not a part of the stent when each of the first and second image type is dark; or the corresponding portion of the assembly is a part of the stent when the first image type is dark and the second image type is bright.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the various embodiments of the present invention only, and are presented for providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

The above and further advantages of the invention may be better understood by referring to the following description in conjunction with the accompanying drawings in which.

DETAILED DESCRIPTION

It is to be understood that the present invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is further appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Figure 1:
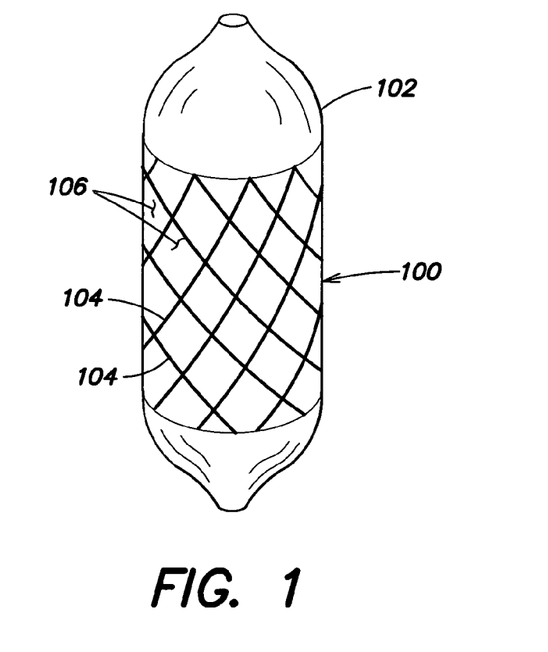
FIG. 1 is a perspective view of a stent mounted on a supporting structure.

As shown in FIG. 1, a stent 100 is mounted on a supporting structure 102. The supporting structure 102 may be a mandrel or a balloon of a balloon catheter on which the stent 100 is mounted. In either embodiment, the supporting structure 102 is made from a transparent or light diffusing material, e.g., glass, plastic, etc. In the case of a balloon-mounted stent, a rigid catheter shaft (not shown) is provided on which the balloon catheter would be positioned.

The stent 100 includes stent struts 104 defining interstitial spaces 106. As shown, the interstitial spaces 106 reveal the surface of the supporting structure 102 between the stent struts 104.

In one embodiment, the supporting structure 102, i.e., either the mandrel or the balloon catheter, is rotatable so that fully 360° about the stent can be imaged, as will be discussed below. The rotation of the supporting structure 102 is under the control of a coating apparatus, for example, one described in U.S. Pat. No. 6,645,047, the subject matter of which is hereby incorporated by reference in its entirety.

Figure 2A:
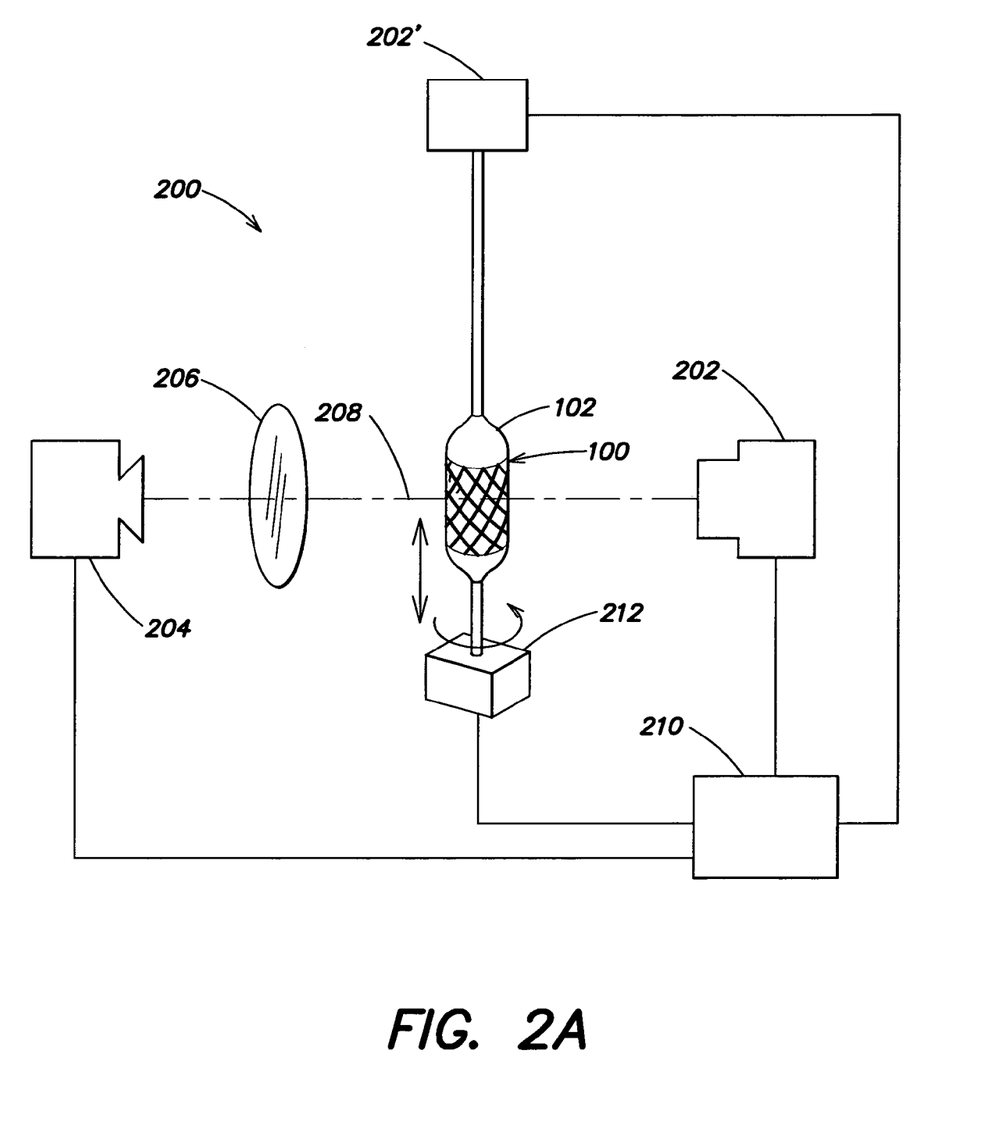
FIGS. 2A and 2B are block diagrams of one embodiment of the present invention.
Figure 2B:
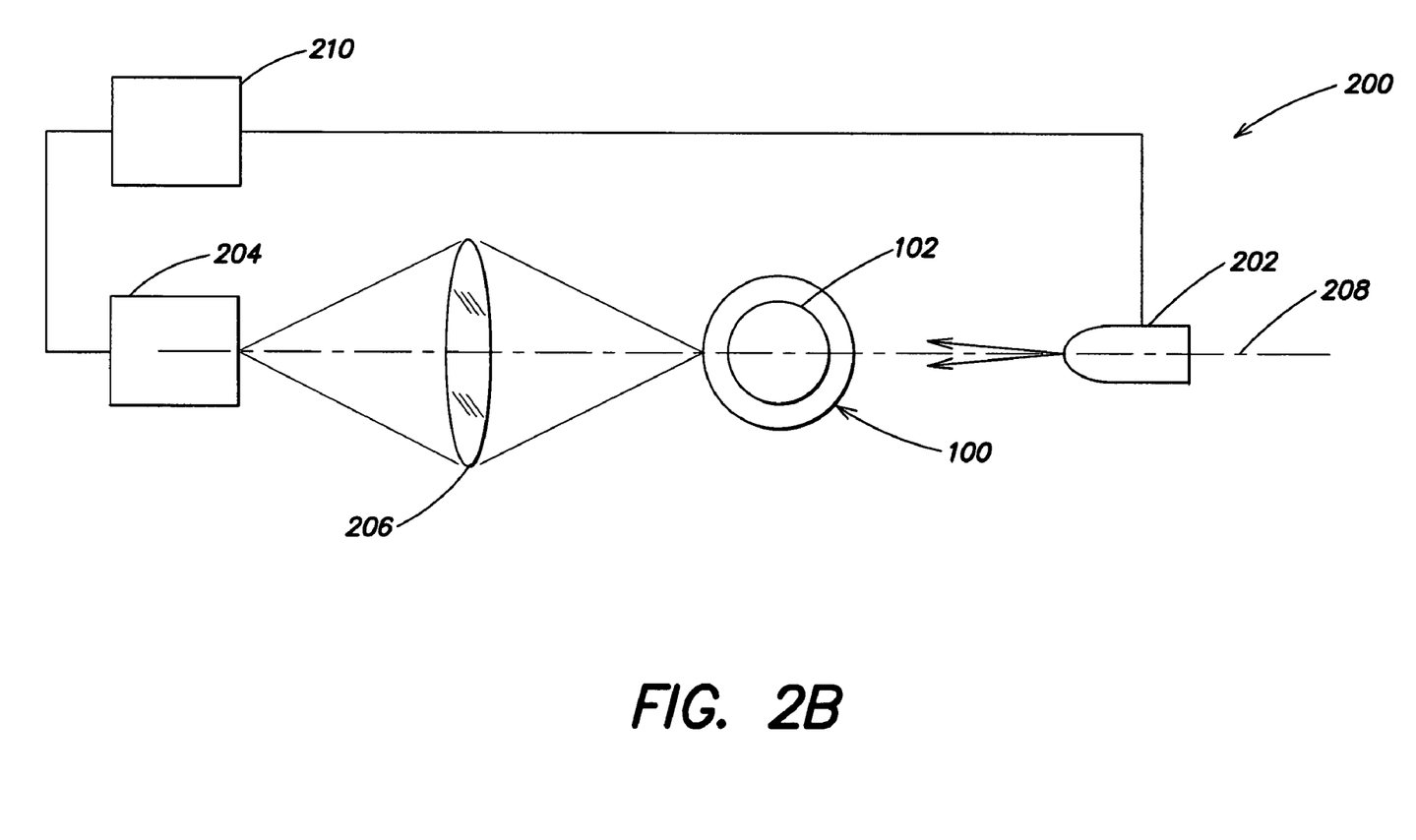

In one embodiment of the present invention, a back lighting system 200 is provided as shown in perspective in FIG. 2A and from above in FIG. 2B. The back lighting system 200 includes a light source 202, an image capturing apparatus, e.g., a camera 204, and an imaging lens 206. The stent 100 is positioned between the camera 204 and imaging lens 206 and the light source 202. Thus, from a perspective of the camera 204, the light from the light source 202 is coming from behind the stent 100. The camera 204, the imaging lens 206, the stent 100 and the light source 202 are linearly aligned along an optical axis 208 along which the light from the light source 202 is also directed. In one embodiment, the imaging lens 206 is about 15-25 mm from the stent 100.

The image capturing apparatus or camera 204 includes a light sensitive device such as a CCD area camera, a CCD line camera, a high-resolution CMOS area camera, or any known device or devices that can capture transmitted, reflected or scattered light. An example of an image capturing device or camera 204 is the Model TM-2016-8 CCD progressive scan camera from JAI PULNiX, Inc. of San Jose, Calif.

A processing system 210, e.g., a personal computer under software control, is coupled to the image capturing apparatus 204 to provide control signals, as well as to store any images captured by the camera 204. The light source 202 may be of any type known to one of ordinary skill in the art such as, but not limited to, an LED, fluorescent, incandescent, etc., and is coupled to the processing system 210. As one non-limiting example, a high brightness LED, either white or red, such as model HLMP-EG08-YZ000 from Agilent Technologies, Inc. Palo Alto, Calif. may be used. The imaging lens 206 may either be separate from the camera 204 or incorporated therein. As one non-limiting example, a Rodagon 45/50 imaging lens from LINOS Photonics Ltd, Buckinghamshire, United Kingdom may be used. One of ordinary skill in the art will understand the properties required of the imaging lens 206 for capturing an image by the camera 204.

The supporting structure 102 with the stent 100 mounted thereon is positioned on an application base 212 that is coupled to the processing system 210. Under control of the processing system 210, the application base 212 functions to rotate and/or move the supporting structure 102 up and down. In addition, the processing system 210 can control movement of the camera or imaging system 204 and the light source 202.

By combination of linearly moving and/or rotating the supporting structure 102, in addition to movement of the image capturing apparatus 204 and the light source 202, the strut surfaces of the stent 100 can be illuminated and their images captured. Under control of the processing system 210, sections of the strut surfaces of the stent 100 can be captured and the corresponding images used to locate the stent on the supporting structure 102 for subsequent procedures, for example, coating application.

The image of the stent 100 is created by differentiating between the stent strut 104 and its background, i.e., the supporting structure 102, based on light intensity differences. If the strut 104 emits a low light level while the background, i.e., the supporting structure 102, emits a high light level, the strut 104 will appear to the camera 204 as being darker or black and the background will appear lighter or white.

Figure 3:
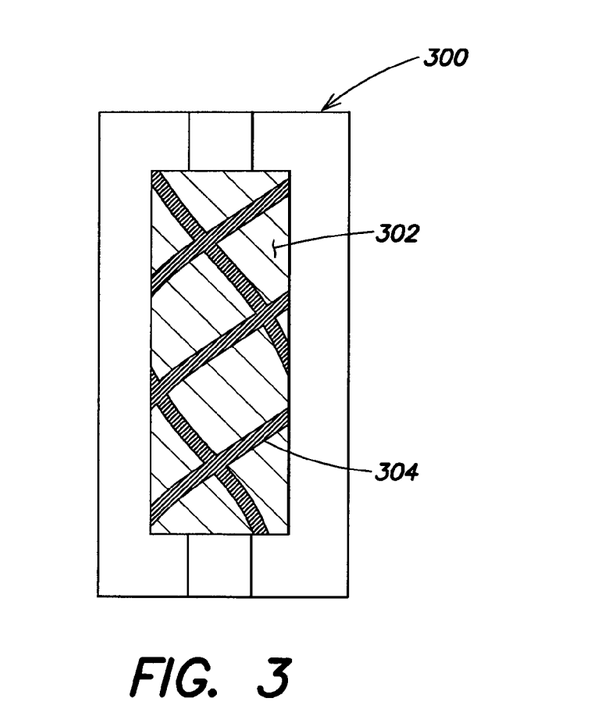
FIG. 3 is an image of a stent captured as per the embodiment shown in FIGS. 2A and 2B.

As shown in FIG. 3, an image 300 captured by the camera 204 shows a strut image 304 as being darker than a supporting structure image 302 that would show through the interstitial spaces 106 of the stent 100.

The light from the light source 202 passes through the interstitial spaces 106 from the side on which the light source 202 is positioned and penetrates the supporting structure 102. Using the diffusing or transparent properties of the supporting structure 102 as a light guide, the light from the light source 202 will be scattered to the camera 204. Light will be scattered only from portions of the supporting structure 102 that are not covered by a strut 104 of the stent 100.

In an alternate embodiment, a light source 202' may be used to provide light from within the supporting structure 102 or the light is provided to emanate from within the supporting structure 102. Fiber optic cable or other light guide material may be used to provide light from within the supporting structure 102. The mechanism for providing this light from within would be understood by one of ordinary skill in the art as well as how a single light source could be used to provide light from within and/or from behind the supporting structure 102.

Of course, whether the light source 202 is behind the stent to provide light or providing light from within the supporting structure 102, the light must be bright enough to create the desired contrast between the strut 104 and the interstitial spaces 106. Further, the intensity must not be so bright as to saturate the camera 204.

Advantageously, the backlight system 200 will provide an image that distinguishes between the stent 100 and the supporting structure 102 irrespective of the material, texture and surface finish of the strut 104. Thus, mechanical irregularities introduced by, for example, crimping the stent 100 onto a balloon of a balloon catheter will not affect the system's ability to detect the edges of the stent struts.

Figure 4:
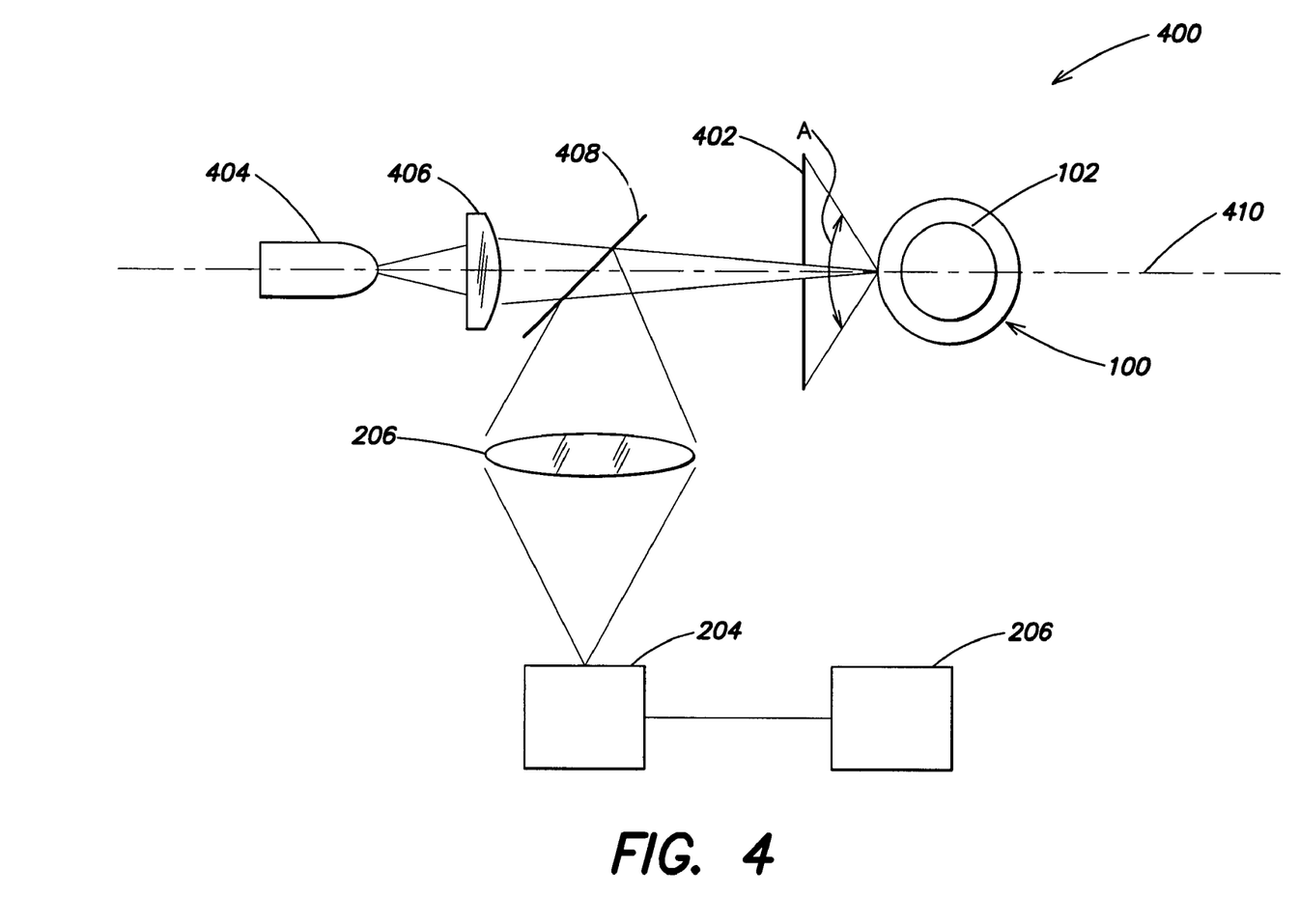
FIG. 4 is a block diagram of another embodiment of the present invention.

In another embodiment of the present invention, as shown in FIG. 4, a front lighting system 400 includes a diffusive light source 402 and a reflective light source 404. The reflective light source 404 provides light energy through a reflective light lens 406 and then through a beam splitter 408. The light from the reflective light source 404, reflective light lens 406, and beam splitter 408 follows a light axis 410 through the diffusive light source 402 to impinge upon the stent 100 and the supporting structure 102. An imaging lens 206 is positioned to receive the light reflected from the stent 100 and the supporting structure 102 and directed toward the camera 204 by the beam splitter 408 for capture.

There is an opening, i.e., a gap, in the diffusive light source 402. The light from the reflective light source 404 travels through the gap from the beam splitter 408. The light that is reflected back from the stent 100 and the supporting structure 102 travels back through that same gap. As a result of the direct light traveling through the gap, the stent 100 and the supporting structure 102 receive a full "sky" of light made from the light from the reflective light source 404 and the light from the diffusive light source 402.

Figure 5:
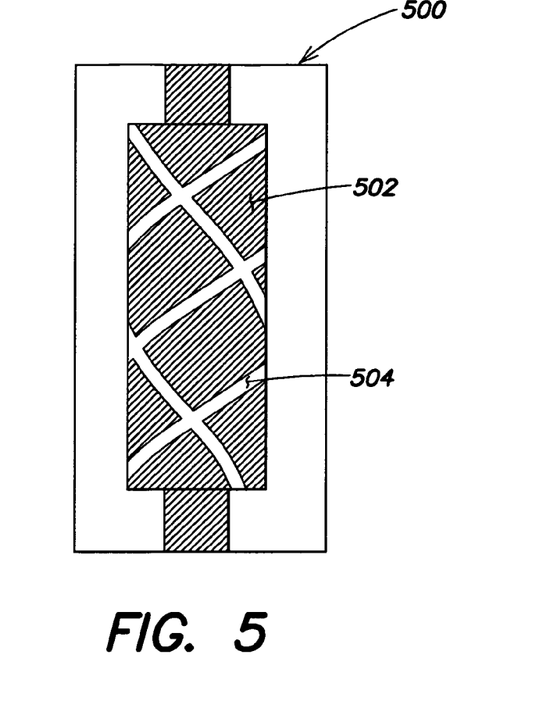
FIG. 5 is an image of a stent captured as per the embodiment shown in FIG. 4.

The reflective light source 404 can be of any kind, for example, but not limited to, an LED, fluorescent, incandescent, etc. The image is created by differentiating between a strut 104 and the background, i.e., the supporting structure 102, based on light intensity differences. As shown in FIG. 5, an image 500 captured by the camera 204 shows that the strut 104 emits a high light level 504 that shows as white on a dark background 502 that shows as being darker or black.

In an alternative version of the front lighting system 400, the reflective light source 404 and reflective light lens 406 may be switched with the camera 204 and imaging lens 206 relative to the beam splitter 408.

Still further, a light diffuser may be inserted between the reflective light lens 406 and the reflective light source 404.

Figure 7:
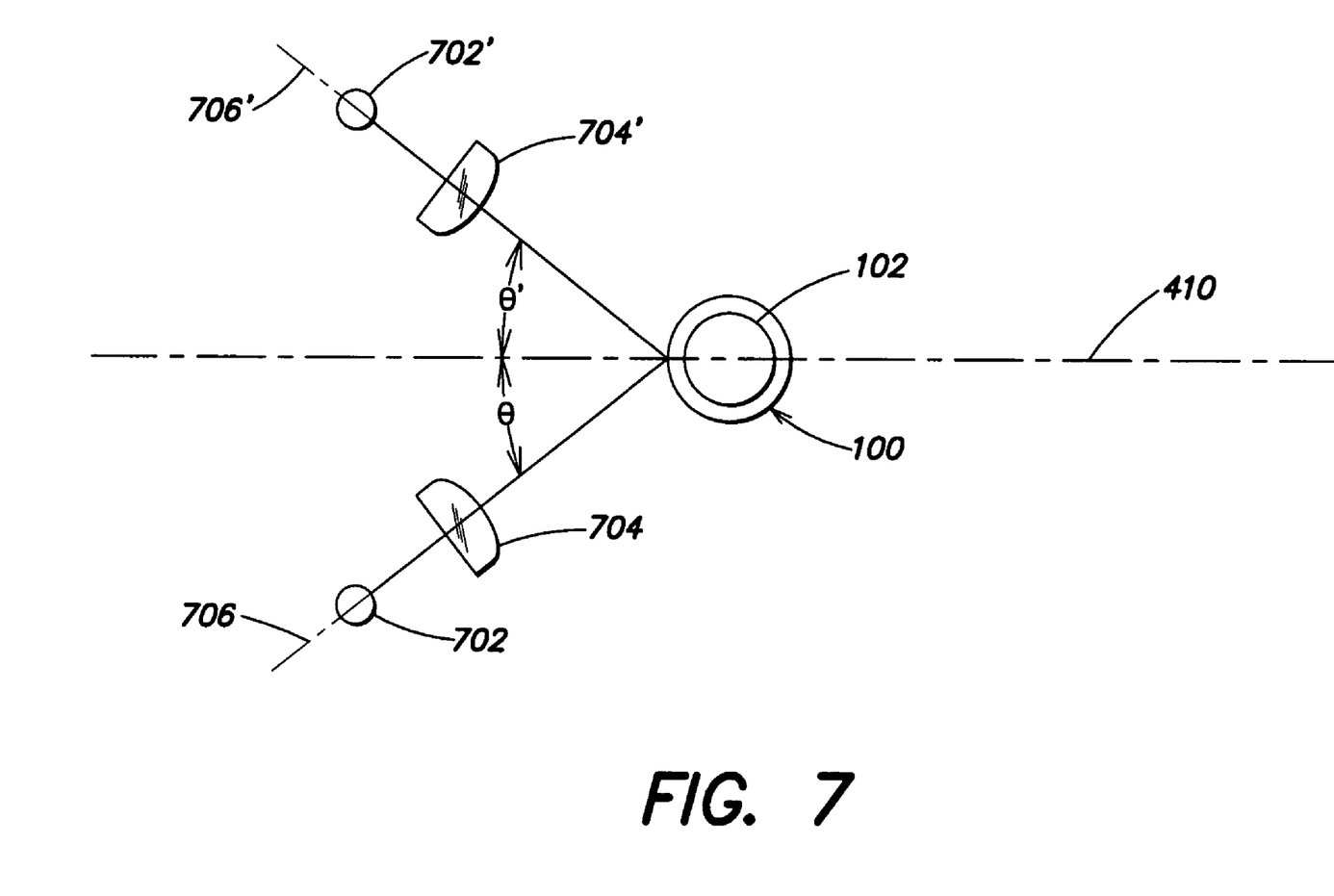
FIG. 7 is a block diagram of an alternate embodiment of a diffuse light source.

The diffusive light source 402 can be of any type known to one of ordinary skill in the art, for example, but not limited to, an LED, fluorescent, light-emitting foil, LCD backlight, etc. A white electroluminescence backlighting panel from Edmund Industrial Optics of Barrington, N.J. may be used. The beam splitter may be a mirror-type beam splitter, 50%× 50%, also available from Edmund Industrial Optics The diffusive light source 402 may also be implemented, as shown in FIG. 7, by two separate light sources 702, 702' and two respective light lens 704 and 704' that provide light energy along two respective light axes 706, 706' at symmetric angles $\theta$, $\theta'$ with respect to the light axis 410.

The light intensities of the reflective light source 404, the diffusive light source 402 and the light sources 702, 702' can be individually controlled.

As shown in FIG. 4, the diffuse light source 402 provides an angle of coverage A in the range of 80°-120°. This angular coverage A, advantageously, allows the present invention to image a large range of types of stents, for example, those stents with small strut width, tight strut corners and varying strut texture, to capture an image of the edges of the stent struts 104. The angular coverage A provides light that hits, on a tangent, relative to the curved portion of a stent edge. Thus, the diffuse light source 402 will provide an image of one stent edge for detection by the camera 204.

Figure 6:
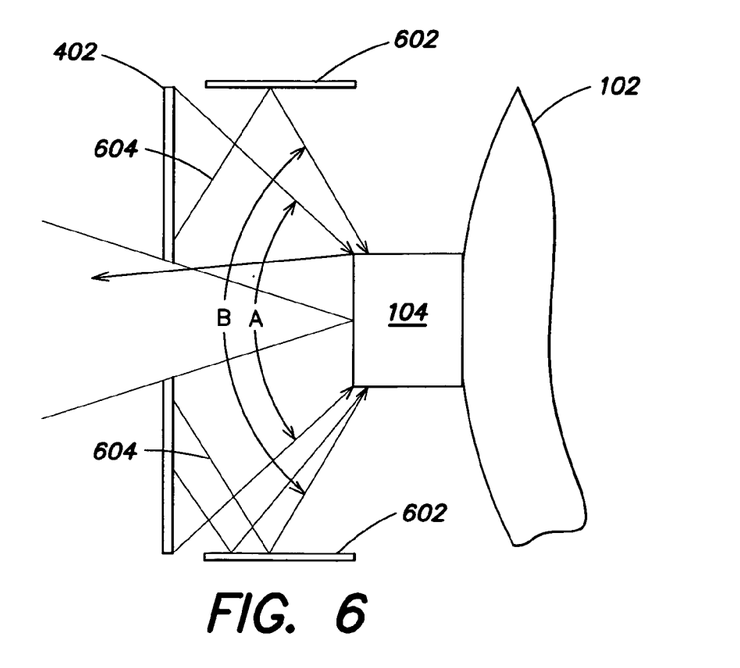
FIG. 6 is a block diagram of one embodiment of a lighting system using a diffuse light source.

In another embodiment of the present invention, the illumination angle is increased by providing additional mirrors to the system shown in FIG. 4. Two side mirrors 602 are added to the light system 400, as shown in FIG. 6. The side mirrors 602 are stationary, but adjustable, and substantially parallel to the light axis 410. The side mirrors 602 reflect higher angle light rays 604 coming from the diffusive light source 402 and provide a larger illumination angle B in the range of 140°-170° symmetrically disposed about the optical axis 410 and nominally 140°-150°. The illumination angle B is a function of a distance between the opposing side mirrors 602 and an angle at which the light impinges on the stent 100 and the supporting structure 102. The reflection of the higher angle light rays 604 provides the present invention with the ability to generate an image from even very thin crimped strut stents. One of ordinary skill in the art will understand that each of the side mirrors 602 may comprise multiple mirrors and that the side mirrors 602 may be mounted in such a way that the position of the mirror can be adjusted as necessary.

The addition of the side mirrors 602 provides for the larger illumination angle B and therefore provides greater illumination under which an image of the mounted device can be captured. There may be instances, however, where a portion of the mounted device, i.e., a stent strut, appears dark in the image and which would then be, incorrectly, identified as not a part of the stent. This is likely to happen with stents that are crimped onto a balloon portion of a balloon catheter as the crimping process can result in convoluted strut positions.

To more accurately identify portions of the stent, in accordance with one embodiment of the present invention, a method is provided for integrating pixels from successive, but phase or angularly offset, captured images of the mounted stent 100, The images relate to the same position on the mounted device and are combined, or compared, to arrive at a single representation of the reflection from that point.

Initially, the imaging system is calibrated with respect to its field of view such that a pixel captured in an image corresponds to a specific physical location in the system. Thus, a specific pixel location as defined by a height along the stent axis at a particular angle of rotation around the stent axis, in one captured image will correspond to that same pixel location in any other captured image. Because the image capturing device captures a portion of the device's image, there is an angular component that must be calculated and accounted for. Further, because each pixel corresponds to a known location, the same physical location from one captured image to another can be identified if the offsetting rotational angle between the two images is known. A mechanism and method for calibrating an imaging system is disclosed in U.S. patent application Ser. No. 10/982,408 which is hereby incorporated by reference in its entirely.

Figure 8:
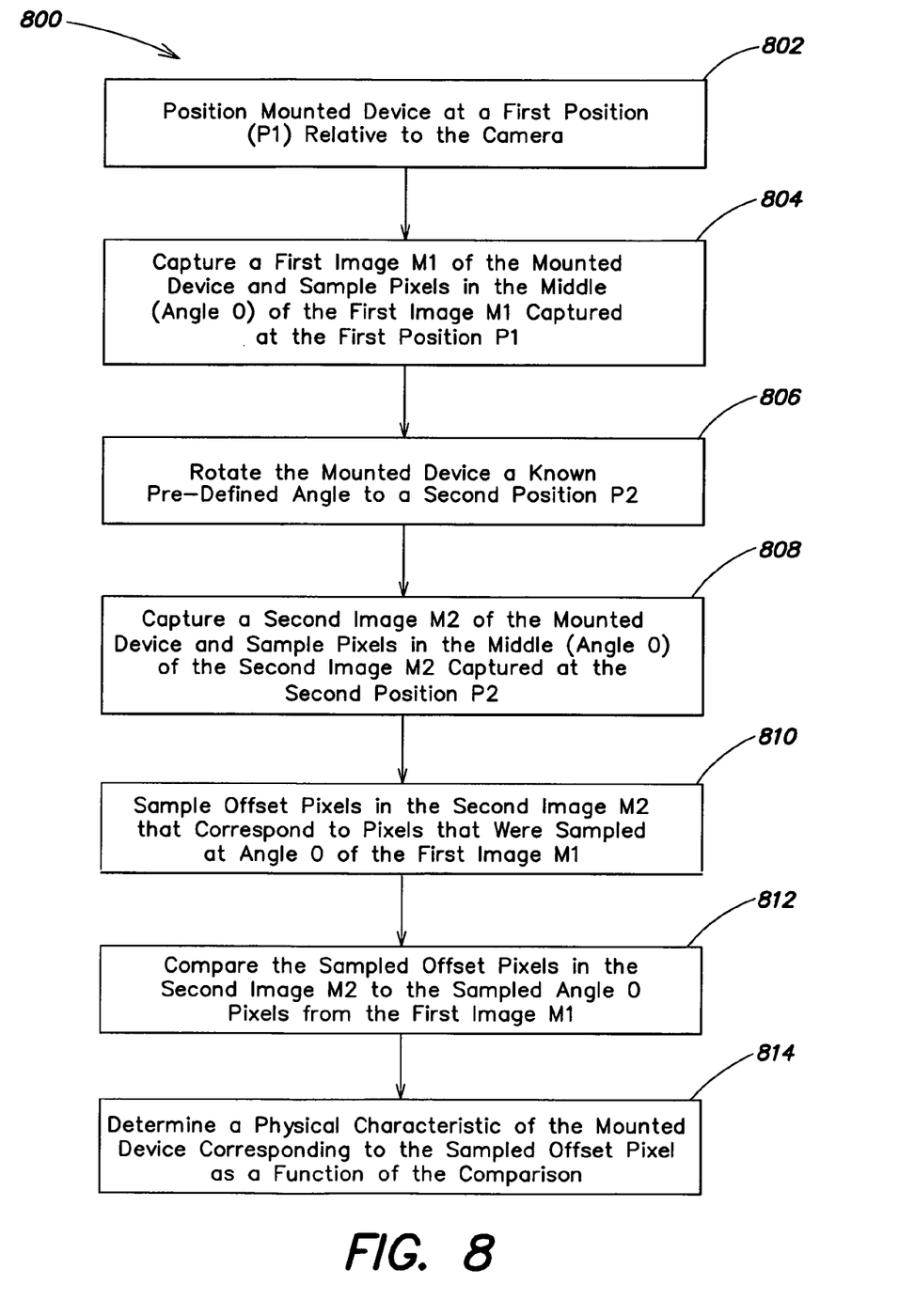
FIG. 8 is a method according to an embodiment of the present invention.

In accordance with the method of integration, pixels from a series of successive and overlapping images, which are related to one another due to calculations as to the same positions on the scanned surface, are combined into a single representation of the reflection from a particular point, In accordance with a method 800 as shown in FIG. 8, a device is mounted and positioned at a first position P1 relative to the camera 204 in step 802. A first image M1 of the mounted device is captured and pixels in the middle, i.e., at an angle 0 (zero) or along the optical axis, of the first image M1, are captured in the first position P1, step 804. As the camera 204 used in one embodiment is an area camera, the middle, or angle 0 portion, of the captured image is sampled. It should be noted, however, that while only the middle of the captured image is used, other portions of the mounted device are also captured in each image.

Next, step 806, the mounted device is rotated a known or predetermined angle to a second position P2. A second image M2 is captured, step 808, and the pixels in the middle, i.e., at angle 0, of the second image M2 are captured. At step 810, while the mounted device is at the second position P2, offset pixels in the second image M2 that may correspond to the pixels that were sampled at angle 0 of the first image M1 are now sampled, step 810. Rotating the mounted device, i.e., the stent 100, changes the position of the stent 100 and the stent's struts 104 relative to the lighting system. As a result of this movement, light may now fall on portions of a strut 104 in the second position P2 whereas, those same portions were dark in the first position P1.

As the rotation angle, i.e., the difference between the first position P1 and the second position P2 is known, and each pixel in an image corresponds to a known location over the mounted device, the two images of the same location can be compared, step 812. By virtue of this comparison, and applying some logic rules in accordance with one embodiment of the present invention, step 814, the combination or comparison of the two or more pictures results in a more accurate image.

As an example, when a particular portion, i.e., part of an image determined by one or more pixels, is dark in both pictures, it is concluded that there is no metal at that location and thus there is no portion of a stent 100 located there. When a pixel representative of the same location is captured in two images, and is bright in each image, it is concluded that the location is metal and is therefore a portion of the stent 100, i.e., a strut 104. Finally, where a pixel representative of a same location is bright in one captured image and dark in another, the conclusion is that the particular location is metal and, therefore, a portion of the stent. The foregoing process is not limited to the integration of only two images but can be applied over any number of images up to a point where no new data is being added.

As described above, the present invention provides light to allow for an accurate image of a device, as above, a stent mounted on a balloon, to be captured. The image captures the details of the stent, i.e., the edges of the stent's struts. Once captured, the image can be used by a coating deposition apparatus to identify the locations on which a coating will be applied. Thus, coating will only be applied in desired locations, e.g., on the stent, and not on the balloon.

Embodiments of the above-described invention may be implemented in either all software, all hardware, or a combination of hardware and software, including program code stored in a firmware format to support dedicated hardware. A software implementation of the above described embodiment (s) may comprise a series of computer instructions either fixed on a tangible medium, such as a computer readable media, e.g. diskette, CD-ROM, ROM, or fixed disk, or transmittable to a computer system in a carrier wave, via a modem or other interface device. The medium can be either a tangible medium, including but not limited to optical or analog communications lines, or may be implemented with wireless techniques, including but not limited to microwave, infrared or other transmission techniques. The series of computer instructions whether contained in a tangible medium or a carrier wave embodies all or part of the functionality previously described herein with respect to the invention. Those skilled in the art will appreciate that such computer instructions can be written in a number of programming languages for use with many computer architectures or operating systems and may exist in machine executable format. Further, such instructions may be stored using any memory technology, present or future, including, but not limited to, semiconductor, magnetic, optical or other memory devices, or transmitted using any communications technology, present or future, including but not limited to optical, infrared, microwave, or other transmission technologies. It is contemplated that such a computer program product may be distributed as a removable media with accompanying printed or electronic documentation, e.g., shrink wrapped software, preloaded with a computer system, e.g., on system ROM or fixed disk, or distributed from a server or electronic bulletin board over a network, e.g., the Internet or World Wide Web.

Further, with respect to the control system 210, it is envisioned that the control system 210 could be implemented as a computer.

The control system 210, in one embodiment of the present invention, is a general purpose personal computer or computing device implementing one or more application programs to control and interact with the camera 204, the applicator base 212 and the light source 202. The computer may run an operating system as is known, such as, Microsoft Windows, UNIX, Linux or AppleOS. The application programs may be a combination of commercially-available programs or programs written in any one of a number of available programming languages including, but not limited to, C, C++, Java, Perl, and Fortran.

Figure 9:
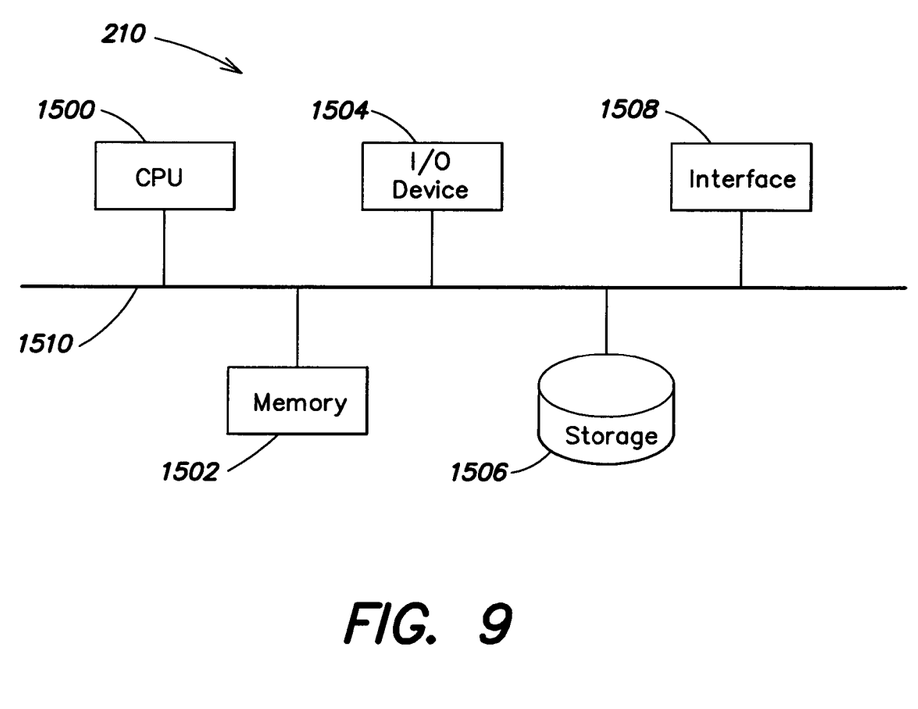
FIG. 9 is a block diagram of a computing device.

The computer, as above, can be any one of a number of devices, however, these devices have some components and/or functionality in common, irrespective of their relative technical complexities. As shown in FIG. 9, a computing device includes a central processing unit 1500, a memory 1502, an input/output device 1504, for example, a keyboard, key pad or touch screen, storage 1506, for example, a hard disk drive, and an interface 1508 for communicating to a network. A bus 1510 couples these devices to one another to allow communication between them.

Although various exemplary embodiments of the present invention have been disclosed, it will be apparent to those skilled in the art that various changes and modifications can be made which will achieve some of the advantages of the invention without departing from the spirit and scope of the invention. It will be apparent to those reasonably skilled in the art that other components performing the same functions may be suitably substituted. Accordingly, it is intended to embrace all such alternatives, modifications and variations that fall within the spirit and scope of the appended claims.

What is claimed is:

1. A system, comprising:
a supporting structure;
an item mounted on the supporting structure;
a beam splitter;
a direct light source to direct light along a light axis through the beam splitter to illuminate the supporting structure and the mounted item;
a second light source to illuminate the supporting structure and the mounted item with diffuse light, the second light source positioned to provide the diffuse light symmetrically about the light axis;
a first mirror;
a second mirror disposed opposite the first mirror and symmetrically about the light axis, the first and second mirrors reflecting higher angle diffuse light from the second light source onto the item and the supporting structure; and
an image capturing apparatus positioned to capture light reflected by the beam splitter, the light provided to the image capturing apparatus being light reflected by the mounted item and the supporting structure back along the light axis.

2. The system of claim 1, wherein;
an angle of coverage of the second light source is in a range of 80° to 120°.

3. The system of claim 1, wherein:
the mounted device is a stent; and
the supporting structure is a balloon catheter having a balloon portion on which the stent is mounted, the balloon portion comprising a light diffusing material.

4. A method, comprising:
mounting a device on a supporting structure;
directing a first type of light from a first light source along a light axis through a beam splitter to illuminate the supporting structure and the mounted item, the first type of light being direct light;
illuminating the supporting structure and the mounted item with a second type of light from a second light source, the second type of light being provided symmetrically about the light axis, the second type of light being diffuse light;
disposing a second mirror opposite a first mirror symmetrically about the light axis;
reflecting higher angle diffuse light from the second light source onto the item and the supporting structure; and
capturing an image of light directed by the beam splitter, the directed light being light reflected by the mounted item and the supporting structure back along the light axis.

5. The method of claim 4, wherein;
the first type of light is directed toward the supporting structure and the mounted item at a first angle with respect to the light axis; and
the second type of light is directed toward the supporting structure and the mounted item at a second angle with respect to the light axis,
wherein the first angle is less than or equal to the second angle.

6. The method of claim 4, wherein:
an angle of coverage of the second light source is in a range of 80° to 120°.

7. A method of determining characteristics of a portion of a mounted device assembly, the mounted device assembly comprising a device mounted on a support structure, the method comprising:
capturing a first image of the assembly at a first angular position;
storing a central portion of the first image;
rotating the assembly a predetermined angular amount to a second angular position;
capturing a second image of the assembly at the second angular position;

identifying pixels in the second image that correspond to pixels in the central portion of the first image, the identified pixels in the second image being of a first image type;

comparing the identified pixels in the second image to the corresponding pixels in the central portion of the first image, the corresponding pixels in the central portion of the first image being of a second image type, the identified pixels in the second image and the corresponding pixels in the central portion of the first image each corresponding to a same portion of the assembly; and determining that the corresponding portion of the assembly is a part of a stent mounted on a balloon portion of a balloon catheter when each of the first and second image type is bright;

determining that the corresponding portion of the assembly is not a part of the stent when each of the first and second image type is dark; and determining that the corresponding portion of the assembly is a part of the stent when the first image type is dark and the second image type is bright.

8. A system for determining characteristics of a portion of a mounted device assembly, the mounted device assembly comprising a device mounted on a support structure, the system comprising:

means for capturing a first image of the assembly at a first angular position;

means for storing a central portion of the first image captured by the capturing means;

means for rotating the assembly a predetermined angular amount to a second angular position;

means for capturing a second image of the assembly at the second angular position;

means for identifying pixels in the second image that correspond to pixels in the central portion of the first image, the identified pixels in the second image being of a first image type;

means for comparing the identified pixels in the second image to the corresponding pixels in the central portion of the first image, the corresponding pixels in the central portion of the first image being of a second image type, the identified pixels in the second image and the corresponding pixels in the central portion of the first image each corresponding to a same portion of the assembly; and means for determining that the corresponding portion of the assembly is a part of a stent mounted on a balloon portion of a balloon catheter when each of the first and second image type is bright;

means for determining that the corresponding portion of the assembly is not a part of the stent when each of the first and second image type is dark; and means for determining that the corresponding portion of the assembly is a part of the stent when the first image type is dark and the second image type is bright.

* * * * *

UNITED STATES PATENT AND TRADEMARK OFFICE
CERTIFICATE OF CORRECTION

| | | |
|---|---|---|
| PATENT NO. | : 7,599,727 B2 | Page 1 of 1 |
| APPLICATION NO. | : 11/227767 | |
| DATED | : October 6, 2009 | |
| INVENTOR(S) | : Teichman et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 541 days Delete the phrase "by 541 days" and insert -- by 988 days --

Signed and Sealed this

Eighteenth Day of May, 2010

David J. Kappos
*Director of the United States Patent and Trademark Office*